United States Patent [19]
Miura et al.

[11] Patent Number: 5,596,139
[45] Date of Patent: Jan. 21, 1997

[54] RESONANT LIQUID DETECTING DEVICE

[75] Inventors: Shinsuke Miura, Tokyo; Tsutomu Odagiri, Chiba-ken, both of Japan

[73] Assignee: Yamaichi Electronics Co., Ltd., Tokyo, Japan

[21] Appl. No.: 301,006

[22] Filed: Sep. 6, 1994

[30] Foreign Application Priority Data

Sep. 6, 1993 [JP] Japan ................................. 5-245912

[51] Int. Cl.⁶ ..................................................... G01N 11/10
[52] U.S. Cl. ........................................ 73/54.24; 73/54.41
[58] Field of Search ................................. 73/54.24, 54.26, 73/54.27, 32 A, 54.25, 54.28, 54.31, 54.32, 54.41

[56] References Cited

U.S. PATENT DOCUMENTS

| | | | |
|---|---|---|---|
| 2,668,442 | 2/1954 | Osbourne | 73/54.24 |
| 3,712,117 | 1/1973 | Fitzgerald et al. | 73/54.26 |
| 3,762,429 | 10/1973 | Fitzgerald et al. | 137/92 |
| 3,875,791 | 4/1975 | Fitzgerald et al. | 73/54.31 |
| 4,299,119 | 11/1981 | Fitzgerald et al. | 73/54.28 |
| 4,524,610 | 6/1985 | Fitzgerald et al. | 73/54.25 |
| 4,704,898 | 11/1987 | Thone | 73/54.25 |
| 4,754,640 | 7/1988 | Fitzgerald et al. | 73/54 |
| 4,811,593 | 3/1989 | Miura et al. | |
| 4,905,499 | 3/1990 | Miura et al. | |
| 5,067,344 | 11/1991 | Fitzgerald et al. | 73/54.24 |
| 5,157,962 | 10/1992 | Fitzgerald et al. | 73/54.25 |
| 5,317,908 | 6/1994 | Fitzgerald et al. | 73/54.26 |

Primary Examiner—Hezron E. Williams
Assistant Examiner—Jay L. Politzer
Attorney, Agent, or Firm—Wenderoth, Lind & Ponack

[57] ABSTRACT

A vibration unit which includes a circular direction vibrator, a liquid detector resonated by the circular direction vibrator, and a vibration transmission member for connecting the circular direction vibrator and the liquid detector and being twist vibrated when the liquid detector is resonated. The resonant liquid detecting device includes a mounting member provided at a location including a node of resonance existing in an intermediate portion of the vibration transmission member and is adapted to suspend the vibration unit in a constant position while the opposite ends of the vibration unit operate as free vibration ends.

14 Claims, 3 Drawing Sheets

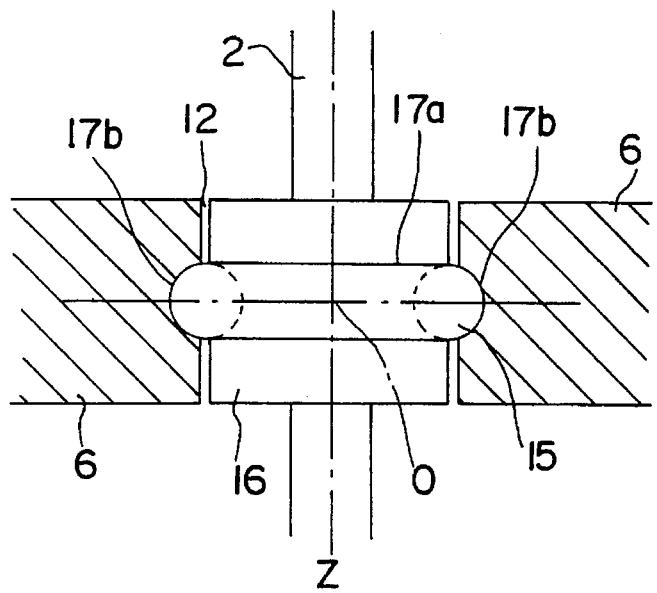
F I G. 2
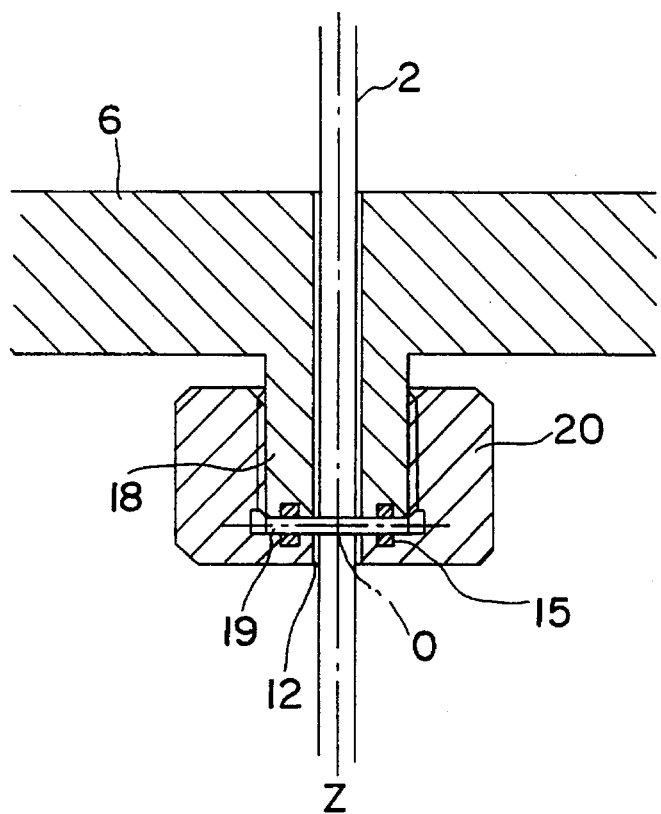
F I G. 3

RESONANT LIQUID DETECTING DEVICE

BACKGROUND OF THE INVENTION

1. Field of the Invention

The present invention relates to a resonant liquid detecting device, which can be used in a viscometer, a density meter, or a liquid-level indicator, and in which a liquid detector, immersed in liquid to be measured, is resonated by a circular direction vibrator made of piezoelectric ceramic.

2. Description of Related Art

U.S. Pat. No. 4,811,593 discloses a vibration unit formed by connecting a vibration shaft directly to a circular direction vibrator and connecting a liquid detector directly to one end portion of the vibration shaft, vibrations of the vibrator being transmitted to the liquid detector through the vibration shaft for resonance.

It is necessary for the vibration unit to be suspended such that the vibration unit is vibration-wise isolated with respect to the casing for receiving a vibrator and a liquid container or liquid feed pipe containing liquid in which the liquid detector is immersed. In the above conventional device, a mass, provided on the end portion of the vibration unit opposite to the liquid detector, is hung on the casing through a vibration absorbing member such as rubber, thereby providing a suspension supporting structure (i.e., a structure for supporting the unit in a suspended fashion).

However, in order to stably hang the upper end (upper side of the vibrator) of the vibration unit with respect to the casing through the mass and to maintain the mass in a stationary state against vibration of the vibrator as in the conventional device, it is required to use a rather large-sized mass having a heavyweight relative to the weight of the overall vibration unit. Therefore, the conventional device has the problem that the overall construction becomes heavy in weight and large in size.

The conventional device can fulfill the requirement of suspending the overall vibration unit by vibration-wise isolating the unit. However, since the mass is substantially connected to the casing, it rigidly restrains (fixes) the vibrator which performs a twist vibration action. The resulting structure turns out to be an external disturbance factor which makes it difficult to obtain a stable and positive twist vibration.

The above problems must also be resolved when viscosity or density of liquid is to be measured by supporting the vibration unit on a liquid container or pipe in a suspending fashion and immersing the liquid detector in the liquid.

SUMMARY OF THE INVENTION

It is an object of the present invention, to provide a resonant liquid detecting device in which active resonance is enhanced even if the unit is firmly suspended on a housing, a liquid container or a pipe through a mounting member, so that a reliable measurement can be obtained by removing an external disturbance factor attributable to the suspended fashion supporting structure.

In order to achieve the above object, there is essentially provided in a resonant liquid detecting device a vibration unit comprising a circular direction vibrator, a liquid detector resonated by the circular direction vibrator, and a vibration transmission member for connecting the circular direction vibrator and the liquid detector and being twist vibrated when the liquid detector is resonated, and a mounting member provided at a location including a node of resonance existing in an intermediate portion of the vibration transmission member and adapted to suspend the vibration unit in a predetermined position so that opposite ends of the vibration unit freely vibrate.

Preferably, the circular direction vibrator and the liquid detector are actuated in a vibration mode which is equivalent to ¼ wavelength from the node of resonance.

Also, an elastic member may be provided on an area between the vibration transmission member and the mounting member.

According to the present invention, the vibration transmission member which performs a twist vibration action is mounted on the casing, the liquid container, or the like through the mounting member. The overall vibration unit is supported in a suspended fashion, and the opposite ends of the vibration unit are freely vibrating ends. Accordingly, there can be provided a reliable liquid detecting device which is capable of enhancing active resonance between the vibrator side and the liquid detector side which are divided by the mounting member. The device is also capable of inducing stable and efficient resonance. Moreover, the inventive device can be firmly secured to a housing, liquid container or pipe by means of the mounting member. And even if the inventive device is firmly secured, the vibration transmission is not adversely affected. In addition, the liquid can be measured with a high degree of precision by removing, as much as possible, an external disturbance factor attributable to the supporting structure.

This inventive device is most suitable for use as a supporting structure of a resonant unit for resonating a liquid detector by a vibrator.

The above and other objects, features and advantages of the present invention and the manner of realizing them will become more apparent, and the invention itself will best be understood from a study of the following description and appended claims with reference to the attached drawings showing some preferred embodiments of the invention.

BRIEF DESCRIPTION OF THE DRAWINGS

FIGS. 2 to 5 are sectional views of different embodiments of the suspended fashion supporting structures of a vibration unit.

DETAILED DESCRIPTION OF THE PREFERRED EMBODIMENTS

Several embodiments of the present invention will be described in detail hereinafter with reference to FIGS. 1 to 6 of the accompanying drawings.

Figure 6:
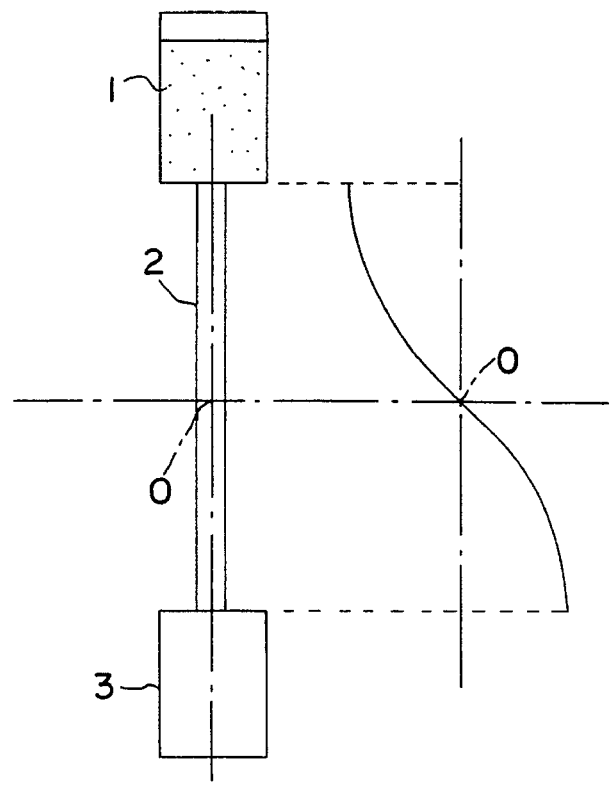
FIG. 6 is a schematic view for explaining a resonant mode of a vibrator and a liquid detector in the vibration unit.

Reference numeral 1 denotes a vibrator vibrating about a vibration axis Z in a circular direction. Directly connected to this vibrator 1 is a vibration transmission shaft 2 coaxial with the circular direction vibration axis Z, and directly connected to one end portion of the vibration transmission shaft 2 is a liquid detector 3 coaxial with the vibration axis Z, thereby constituting a resonant liquid detecting device in which the liquid detector 3 is resonated by means of circular direction vibration of the vibrator 1. At that time, the vibration transmission shaft 2 is reversely vibrated in the circular direction about a node O of resonance as shown in the waveform of FIG. 6. In other words, the vibration transmission shaft 2, as a whole, is twist vibrated about the node O.

It should be appreciated that the vibration transmission shaft 2 is not limited to a shaft member but it may be a plate-like member, a block-like member, a combination thereof, or any other vibration transmission member as long as it can resonate the vibrator 1 and the liquid detector 3.

As mentioned above, the vibrator 1 and the liquid detector 3 are in a so-called resonant relation in which when the vibrator 1 is vibrated about the axis Z in a circular direction, the liquid detector 3 is reversely vibrated in a circular direction. Accordingly, the vibration 1 induces twist vibration, and the vibration is transmitted to the liquid detector 3 through transmission shaft 2. The liquid detector 3 is immersed in liquid 4 which is to be measured, and the viscous resistance and mass inertia of the liquid 4 are detected by means of vibration in the liquid 4.

An acceptable example of the circular direction vibrator 1 is a twist vibrator which ie disclosed in FIGS. 6 and 7 of U.S. Pat. No. 4,811,593, or a twist vibrator which is disclosed in FIGS. 3, 9 and 10 of U.S. Pat. No. 4,905,499. Any of those vibrators can give a circular direction vibration about the axis Z with respect to the transmission shaft 2 and the liquid detector 3.

The vibrator 1 and a large part of a vibration shaft extending from the vibrator 1 are received in a casing 5. One end of the vibration transmission shaft 2 and the liquid detector 3 directly connected to this shaft end are allowed to expose outside be exposed outside of the casing 5.

On that part of the vibration transmission shaft 2 which includes the node O of resonance, a mounting member 6 is mounted. This mounting member 6 is a means for suspending the vibration unit from the casing 5, or a means for suspending the vibration unit on an outer wall 8 of a container 11 or pipe containing the liquid which is to be measured. In the illustrated example, the mounting member 6 acts as a suspending means and also as a cover member attached integrally to the casing and adapted to cover an opening 7 of the casing. At the same time, this mounting member 6 constitutes a cover member for closing a mounting opening 9 of the container 11 or pipe.

In order to have it function as this cover member, the mounting member 6 may be formed of a flange which covers the opening 7 of the casing 5 and annularly expands around the opening 7. A plurality of mounting holes 10 are formed in this flange. The opening 9 is closed by the cover member. The mounting member 6 is firmly secured to the outer wall 8 of the container 11 or pipe by bolts or the like inserted through the mounting holes 10. By doing this, an overall vibration unit can be suspended from the casing 5 at the portion of the transmission shaft 2 including the node O and further on the outer wall 8 of the container 11 or pipe. The present invention may be practiced as a means for suspending the overall vibration unit on the casing 5 by the mounting member 6, or for suspending the overall vibration unit on the liquid containing container 11 or the like.

The end portion of the vibration transmission shaft 2 and the liquid detector 3 mounted on the shaft end are allowed to project outwardly from the casing 5 via a through-hole 12 formed in a central portion of the mounting member 6.

Figure 1:
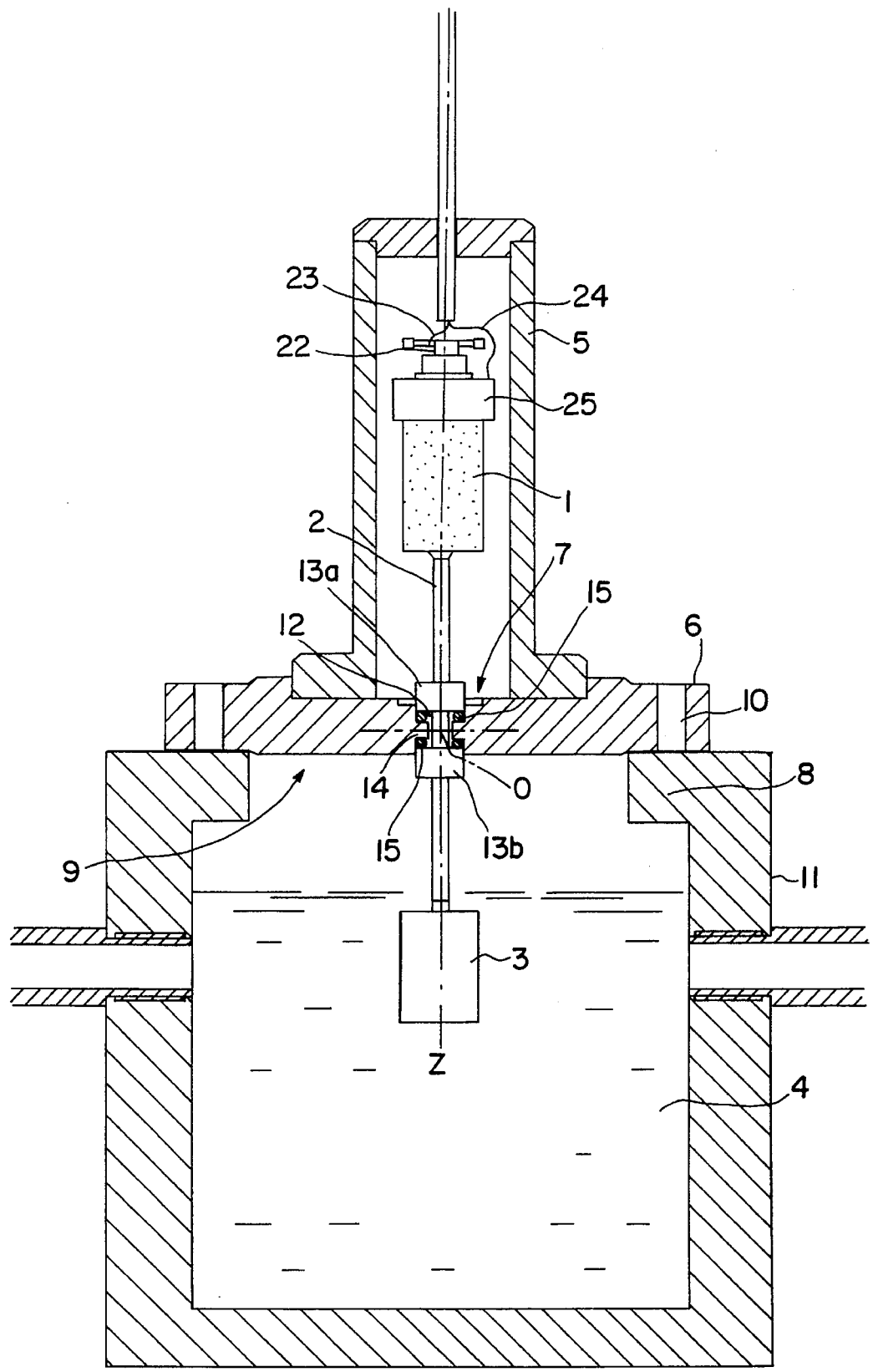
FIG. 1 is a sectional view of a resonant liquid detecting device according to one embodiment of the present invention.

As a means for mounting the mounting member 6 on that part of the transmission shaft 2 which includes the node O existing in an intermediate portion of the transmission shaft 2 which is exemplified as the vibration transmission member, as shown in FIG. 1, that shaft portion of the transmission shaft 2 including the node O projects through through-hole 12 formed in the center of the mounting member 6. On upper and lower portions of the transmission shaft 2 a pair of flange-like upper and lower stoppers 13a and 13b are mounted integrally to the shaft 2 on opposing sides of a projecting wall 14 located on an inner peripheral surface defining the through-hole 12. Compressed elastic rings 15 are each interposed between the lower stopper 13a and the through-hole wall 14 and between the upper stopper 13b and the through-hole wall 14, respectively, so that the vibration transmission shaft 2, i.e., vibration transmission member, is elastically connected to the mounting member 6.

In other words, the elastic rings 15 are provided between the mounting member 6 and the vibration transmission shaft 2. The overall vibration unit is supported on the mounting member 6 in a suspended fashion through the elastic rings 15, and the liquid detector 3 is supported in a suspended fashion through the mounting member 6.

The upper and lower stoppers 13a and 13b are brought into abutment with the surface of the through-hole wall 14 through the elastic rings 15 in order to prevent axial movement of the detection unit and to locate the mounting member 6 in a predetermined position where the node O exists.

Also, as another example, as shown in FIG. 2, a ring-like holder 16 is mounted integrally on that part of the vibration transmission shaft 2 which includes the node O. This ring holder 16 is brought into a sliding fit or loose fit in the through-hole 12. The compressed elastic ring 15 is retained in annular grooves 17a and 17b formed in an outer peripheral surface of ring holder 16 and in an inner peripheral surface defining through-hole 12. By doing this, the vibration unit can be prevented from moving up and down relative to the mounting member 6, and the vibration unit is elastically connected to the mounting member 6 through the elastic rings 15 at an area in the vicinity of the node O.

As a further example, as shown in FIG. 3, a body portion of the mounting member 6 is located in a position offset from the node O. A boss portion 18 having the through-hole 12 and extending along the axis Z is provided at a central portion of mounting member 6. Through this boss portion 18, the mounting member 6 is elastically connected to that part of the vibration transmission member of the vibration unit which includes the node O.

A flange-like up and down axial movement stopper 19 opposing an end face of the boss portion 18 is mounted integrally on that part of the vibration transmission shaft 2 which includes the node O. A nut 20 is attached to the shaft 2 in order to threadedly engage the boss portion 18. By means of nut 20, the upper and-lower movement stopper 19 is fastened tight to the end face of the boss portion 18, thereby compressing elastic rings 15 held on the end face of the boss portion 18. Therefore, the vibration unit is elastically connected to the mounting member 6 at an area in the vicinity of the node O. The elastic rang members 15 may be arranged on upper and lower surfaces of the up and down axial stopper and fastened tight by the nut.

The embodiments shown in FIGS. 1 to 3 illustrate an idea or concept for connecting the mounting member 6 and the vibration unit through an elastic member such as rubber.

The vibration unit is slidably connected to the mounting member 6 for sliding in the rotating direction as in the above exemplified case, or the vibration unit and the mounting member 6 are rigidly connected to each other, although not shown.

As mentioned above, the mounting member 6 for receiving the vibration unit also serves to suspend the overall unit, so that opposite ends of the vibration unit can be free vibration ends.

The vibration unit is freely vibrated at one of its free vibration ends (end on the vibrator 1 side) about the node O as indicated by a waveform of FIG. 6. Similarly, the vibration unit is reversely freely vibrated at the other free vibration end (end on the liquid detector 3 side). A so-called active resonance is induced.

As a free vibration mode in the above resonance, as shown in FIG. 6, the twist vibrator 1 is actuated and the liquid detector 3, through shaft 2, is are vibrated in a vibration mode which is equivalent to ¼ wavelength from the node of resonance. In this respect, the inventive device is significantly different from the conventional device in which only the liquid detector is serves as a free vibration end.

As a modification of the vibration mode, vibrator 1 may be actuated in a vibration mode which is equivalent to N/2 wavelength +¼ wavelength (wherein N is an integral number) from the node O.

Also, the present invention includes a case in which a plurality of nodes O of resonance may be located on an intermediate portion of the shaft 2 as one example of the above-mentioned vibration transmission member, and by selecting one of the nodes O, the mounting member 6 is arranged in the manner as mentioned above.

Figure 4:
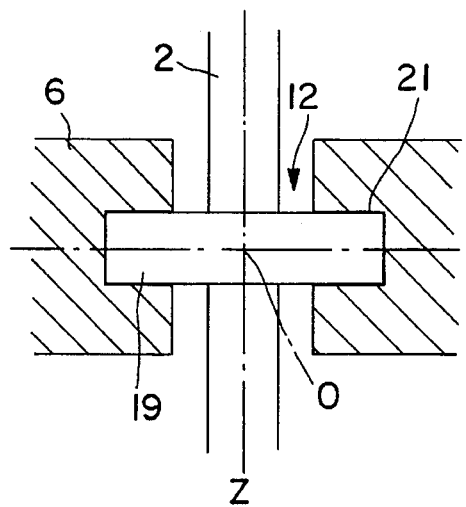
Figure 5:
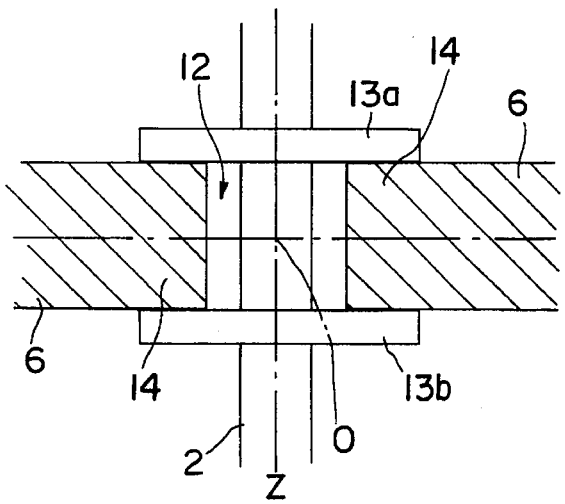

FIGS. 4 and 5 show modified examples of embodiments in which the mounting member 6 is mounted on that part of the vibration unit which includes the node O. According to those modified examples, the mounting member 6 is slidably connected to the vibration unit without a provision of the elastic member as an intermediate member.

As shown in FIG. 4, an upper and-lower movement stopper 19 is mounted integrally on that portion of the vibration transmission shaft 2 which includes the node O. The stopper 19 is brought into sliding fit into an annular groove or recess 21 formed in an inner peripheral surface of the through-hole formed in the mounting member 6.

Also, as shown in FIG. 5, a pair of flange-like upper and lower stoppers 13a and 13b are mounted integrally on the above-mentioned shaft portion, and the stoppers 13a and 13b are arranged in such a manner as to be in abutment with the wall 14 of the through-hole 12 formed in the mounting member 6 in order to prohibit up and down axial movement of the vibration unit.

As will be appreciated from the embodiments of FIGS. 1 to 5, the vibration transmission member and mounting member of the vibration unit are not rigidly connected to each other so that vibration-wise degree of freedom may increase.

The elastic ring members 15 and the mounting member 6 can isolate the liquid, which is to be measured, from the vibrator 1 located inside of the casing 5.

Accordingly, the present invention can be favorably practiced by mounting the inventive deride on a liquid storage tank or pipe, or on an outer wall of a chemical reaction bath in order to normally measure the viscosity, density or surface of the liquid to be measured. Namely, the liquid detector detects the viscosity, density, liquid surface, etc. based on variation of vibration load which is variable in accordance with the kind of liquid and a change in liquid surface.

The vibration transmission shaft 2 refers to a member extending along the vibration axis Z for transmitting the vibration of the vibrator 1 to the liquid detector 3. The vibration transmission shaft 2 may be equal in diameter over the entire length thereof, or a part of the extension portion of the shaft 2 may have an enlarged diameter or a reduced diameter.

In FIG. 1, reference numeral 22 denotes a vibration sensor which is mounted on that end of the vibration unit opposite to the liquid detector 3. When the liquid detector detects the liquid to be measured and the load of the vibrator 1 is changed, the vibrator sensor 22 detects the change in load and outputs a signal corresponding to such detection through a cable 23 to an arithmetic portion. This arithmetic portion may be located in the casing 5.

As in the case with the vibrator 1, the vibration sensor 22 uses, for example, a piezoelectric element driven by voltage which is known in the prior art, and which converts the variation of mechanical vibration (variation of vibration due to change in load received by the liquid detector 3) into an equivalent voltage signal and outputs the same. Voltage is supplied to the vibrator 1 through a cable 24 to induce mechanical vibration (circular direction vibration by twist vibration).

Also, an arrangement is possible in which a mass 25, for balancing a rotational moment between the liquid detector 3 and the vibrator 1, is mounted integrally on that end portion of the vibrator 1 opposite to the liquid detector 3.

According to the present invention, the inventive device can be firmly secured to the housing, the liquid container or the pipe through the mounting member, and even if the device is firmly secured, the vibration transmission is not adversely affected. The liquid can be measured with a high degree of precision by removing, as much as possible, an external disturbance factor attributable to the suspending-fashion supporting structure. That is, there can be provided a reliable liquid detecting device which is capable of inducing active, stable, and efficient resonance between the vibrator side and the liquid detector side separated by the mounting member while appropriately suspending the resonant vibration unit. This inventive device is most suitable for the use as a suspended supporting structure of a resonant unit for resonating the liquid detector by the vibrator.

Although the invention has been illustrated and described with respect to exemplary embodiments thereof, it should be understood by those skilled in the art that various other changes, omissions and additions may be made to the foregoing without departing from the spirit and scope of the present invention. Therefore, the present invention should not be understood as limited to the specific embodiments set out above but to include all possible embodiments which can be embodied within a scope encompassed and equivalents thereof with respect to the features set out in the appended claims.

What is claimed is:

1. A detection device for detecting properties of liquid, said detection device comprising:
   a vibration unit including:
     a vibration transmission shaft having a first end and a second end,
     a circular direction vibrator formed of piezoelectric ceramic connected at said first end of said vibration transmission shaft, and
     a liquid detector connected at said second end of said vibration transmission shaft, wherein said liquid detector and said circular direction vibrator are coaxially connected at said first and second ends of said shaft, and said first and second ends of said shaft are not directly supported; and
   mounting means, elastically connected to an intermediate portion of said transmission shaft at a location which includes a node of resonance, for suspending said vibration unit so that said first and second ends of said unit freely vibrate in opposite directions at a resonant frequency.

2. A detection device as claimed in claim 1, wherein said circular direction vibrator is capable of actuating said vibration unit in a vibration mode which is equivalent to ¼ wavelength from the node of resonance.

3. A detection device as claimed in claim 1, further comprising an elastic member provided between said vibration transmission and said mounting means.

4. A detection device as claimed in claim 1, further comprising an open-ended casing attached to said mounting means and enclosing said first shaft end which is attached to said vibrator, wherein said mounting means serves as a cover for said casing open end.

5. A detection device as claimed in claim 1, wherein said mounting means is a cover member for closing an opening in a liquid container or pipe and for suspending said liquid detector into liquid in the container or pipe.

6. A detection device as claimed in claim 5, wherein said cover member has a periphery and includes a plurality of mounting holes through said periphery thereof.

7. A detection device as claimed in claim 5, further comprising:

an opening through said cover member, said transmission shaft passing through said opening;

an annular wall projecting from an inner wall defining said opening toward said transmission shaft, said projecting wall forming a reduced diameter opening; and upper and lower stoppers attached to said shaft, said stoppers fitting within said cover member opening and having a larger diameter than the diameter of said reduced diameter opening formed by said annular projecting wall.

8. A detection device as claimed in claim 7, further comprising elastomeric members positioned on an upper surface and a lower surface of said projecting wall to elastically connect said transmission member to said cover member.

9. A detection device as claimed in claim 8, wherein said elastomeric members are compressed elastic rings.

10. A detection device as claimed in claim 1, wherein said mounting means comprises a generally planar member having an opening through which said transmission shaft passes, said opening being defined by an inner peripheral surface having therein a groove, said detection device further comprising:

an enlarged diameter section on said transmission shaft, said section having a diameter which is smaller than the diameter of said opening, said section further having a groove in an outer peripheral surface thereof which corresponds to said groove in said inner peripheral surface; and an elastic ring positioned in said grooves and preventing relative axial movement between said transmission shaft and said planar member.

11. The detection device as claimed in claim 1, wherein said mounting means comprises a generally planar member having an opening through which said transmission shaft passes; said detection device further comprising:

an annular projection extending downwardly from the planar member and being aligned with the opening;

a stopper attached to the transmission shaft; and a nut for coupling with said annular projection, said stopper being interposed between said nut and said annular projection.

12. The detection device as claimed in claim 11, further comprising:

a first groove in a lower surface of said annular projection;

a second groove in an inner surface of said nut; and first and second elastic members located in said first and second grooves, respectively.

13. The detection device as claimed in claim 1, wherein said mounting means comprises a generally planar member having an opening through which said transmission shaft passes, said opening being defined by an inner peripheral surface; said detection device further comprising:

a stopper attached to said transmission shaft, said stopper being located at the node;

an annular recess formed in an inner peripheral surface defining said opening, said recess slidably receiving said stopper.

14. The detection device as claimed in claim 1, wherein said mounting means comprises a generally planar member having an opening through which said transmission shaft passes, said device further comprising:

upper and lower stoppers attached to said transmission shaft; and an annular projection extending inwardly from an inner peripheral wall defining said opening, said projection having upper and lower surfaces, said upper and lower surfaces of said projection slidably engaging said upper and lower stoppers, respectively.

* * * * *